the

US006517576B2

(12) United States Patent
Gabbay

(10) Patent No.: US 6,517,576 B2
(45) Date of Patent: Feb. 11, 2003

(54) IMPLANTABLE PATCH PROSTHESIS HAVING ONE OR MORE CUSPS FOR IMPROVED COMPETENCY

(76) Inventor: Shlomo Gabbay, #1 Randall Dr., Short Hills, NJ (US) 07078

( * ) Notice: Subject to any disclaimer, the term of this patent is extended or adjusted under 35 U.S.C. 154(b) by 0 days.

(21) Appl. No.: 09/734,259

(22) Filed: Dec. 11, 2000

(65) Prior Publication Data

US 2002/0072794 A1 Jun. 13, 2002

(51) Int. Cl.$^7$ .................................................. A61F 2/06
(52) U.S. Cl. .................... 623/2.14; 623/2.11; 623/2.16; 623/2.1; 623/912; 33/511; 33/512
(58) Field of Search ................. 623/2.1, 2.11, 623/2.12–2.19, 2.42, 66.1, 909–910, 912–913; 33/511, 512

(56) References Cited

U.S. PATENT DOCUMENTS

| | | | |
|---|---|---|---|
| 4,692,164 A | | 9/1987 | Dzemeshkevich et al. ...... 623/2 |
| 5,545,215 A | | 8/1996 | Duran ........................... 623/2 |
| 5,769,780 A | * | 6/1998 | Hata et al. ..................... 600/36 |
| 5,861,028 A | * | 1/1999 | Angell ........................... 623/2 |
| 5,935,163 A | * | 8/1999 | Gabbay .......................... 623/2 |

OTHER PUBLICATIONS

*Tetralogy of Fallot.* Author and date unknown. Chapter 22. pps. 301–313.
Gundry, Steven R., M.D. *How to Construct a Monocusp Valve.* Advances in Cardiac Surgery, vol. 12. pp. 169–174. Mosby, Inc. 2000. Loma, Linda, California.
Fiane, Arnt, E. *Monocusp Valve in Right Ventricular Outflow Tract.* 1999. Scandinavian University Press. pp. 33–38.
Schamberger MS, et al. Abstract of *Course of Right and Left Ventricular Function in Patients with Pulmonary Insufficiency after Repair of Tetralogy of Fallot*; Pediatric Cardiology. May–Jun. 2000; 21 (3): 244–8.
Gundry Sr. Abstract of *How to Construct a monocusp valve*; Pediatric Cardiology. 2000; 12: 169–74.
Roughneen, et al. Abstract of *The Pericardial Membrane Pulmonary Monocusp: Surgical Technique and Early Results*; Journal of Cardiac Surgery. Sep.–Oct. 1999; 14 (5): 370–4.
Conte, et al. Abstract of *Homograft Valve Insertion for Pulmonary Regurgitation Late after Valveless Repair of Right Ventricular Outflow Tract Obstruction*; Eur. Jorunal Cardiothorac Surgery. Feb. 1999; 15 (2): 143–9.
Eyskens, et al. Abstract of *Homograft Insertion for Pulmonary Regurgitation after Repair of Tetralogy of Fallot Improves Cardiorespiratory Exercise Performance*; Journal Cardiology. Jan. 2000; 15; 85 (2): 221–5.

* cited by examiner

Primary Examiner—David J. Isabella
Assistant Examiner—Urmi Chattopadhyay
(74) Attorney, Agent, or Firm—Tarolli, Sundheim, Covell, Tummino & Szabo L.L.P.

(57) ABSTRACT

A patch prosthesis includes at least one cusp extending from a length of an associated valve wall. An elongated sheet of biocompatible material is attached to the valve wall, such that a portion of the elongated sheet extends beyond an inflow end of the cusp. A measurement system may be employed to measure the size of a patient's native cusp(s), which measurement may be utilized to select a patch prosthesis having an appropriately sized cusp.

24 Claims, 5 Drawing Sheets

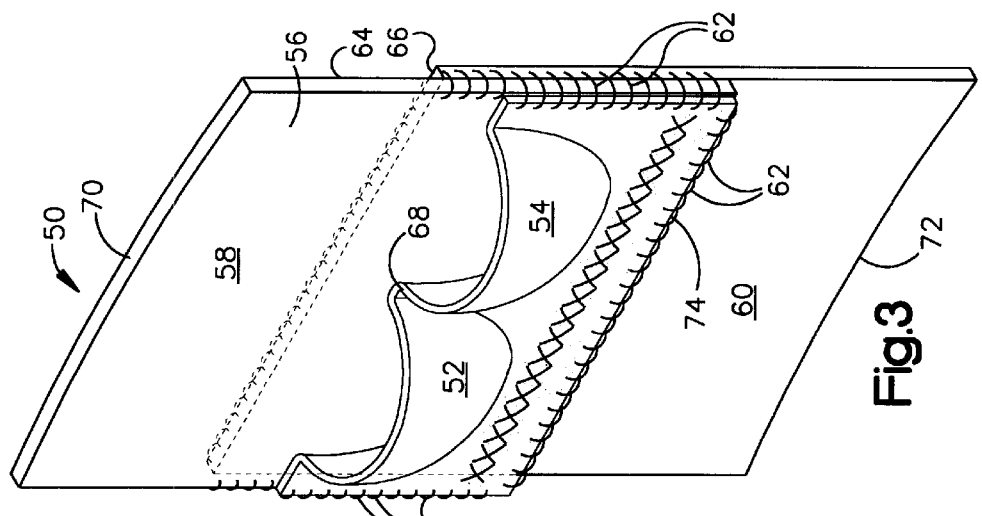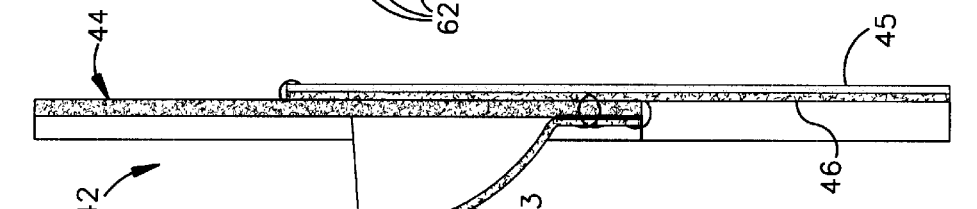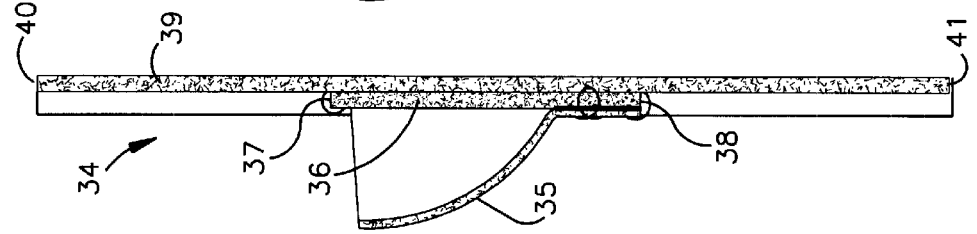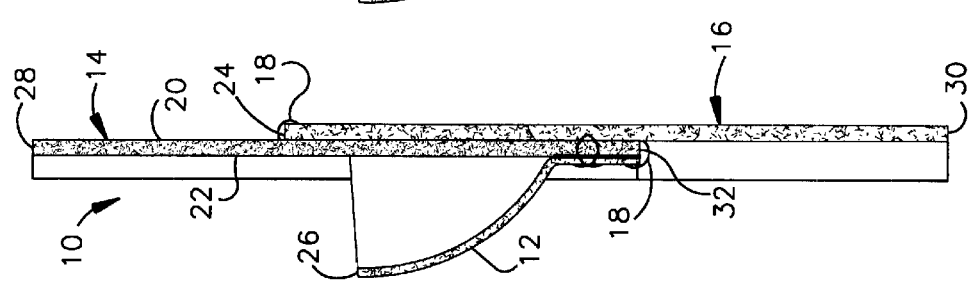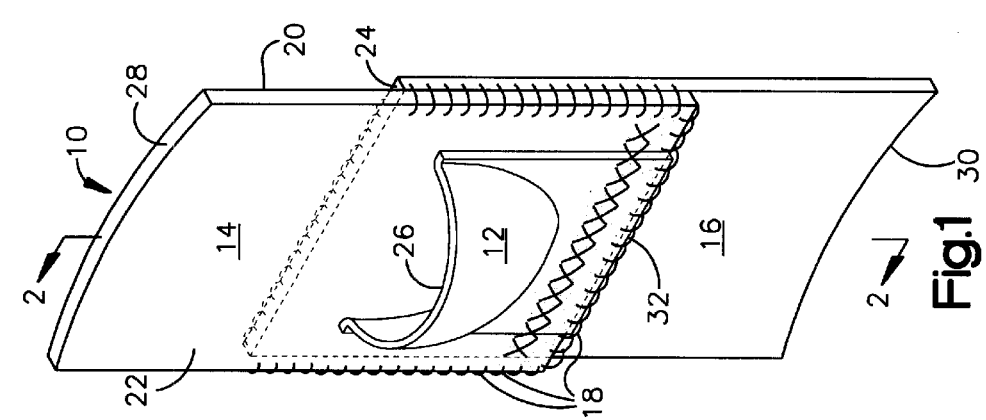

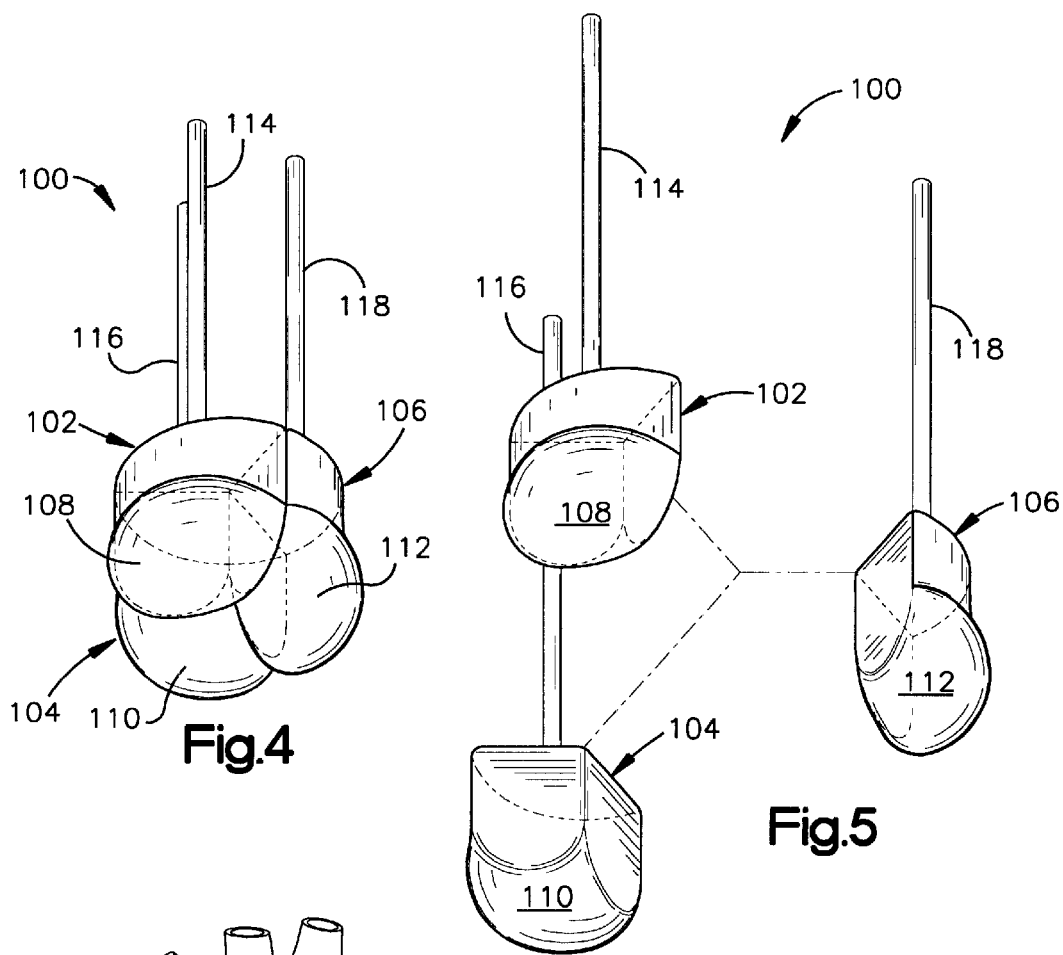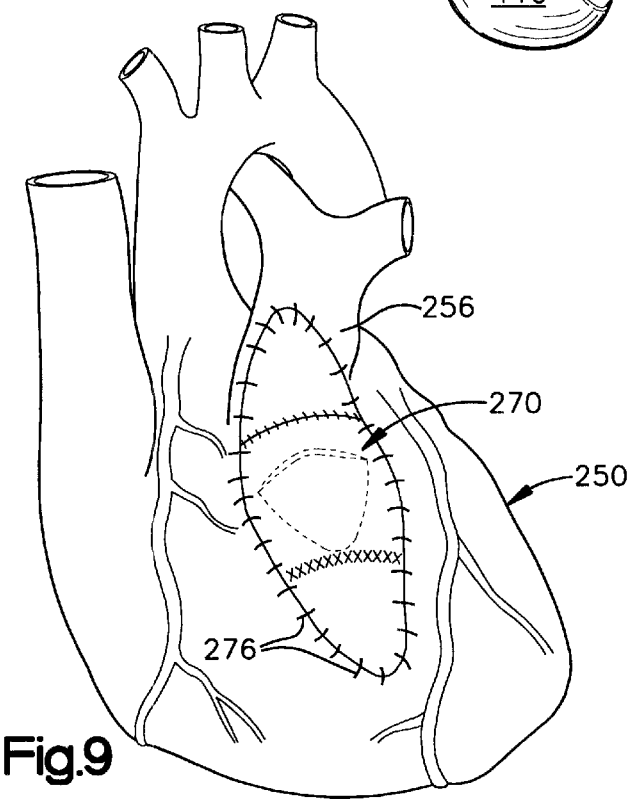

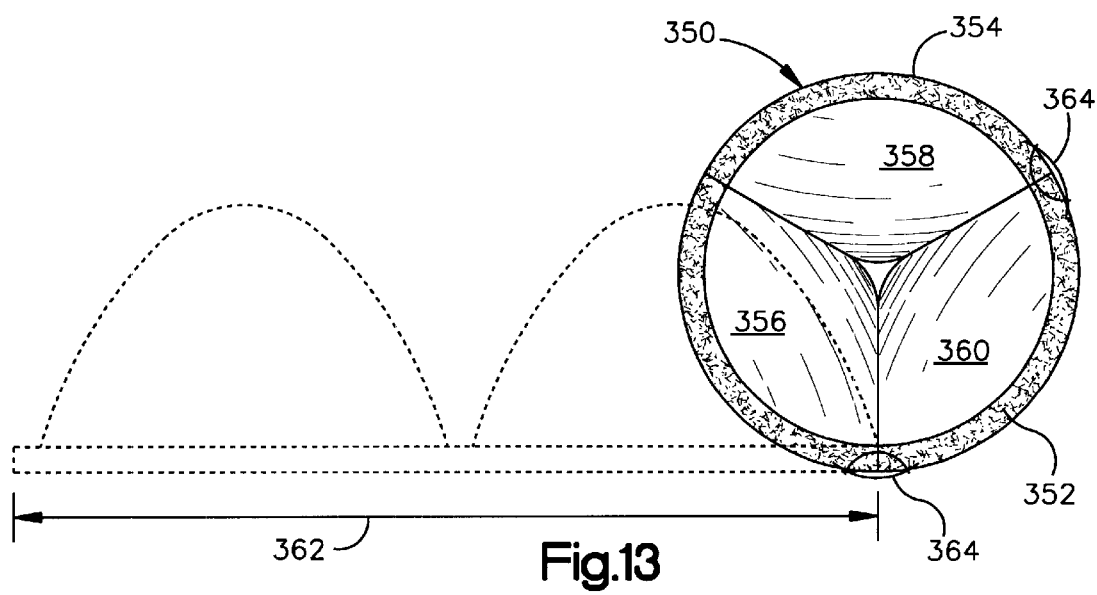
Fig.13
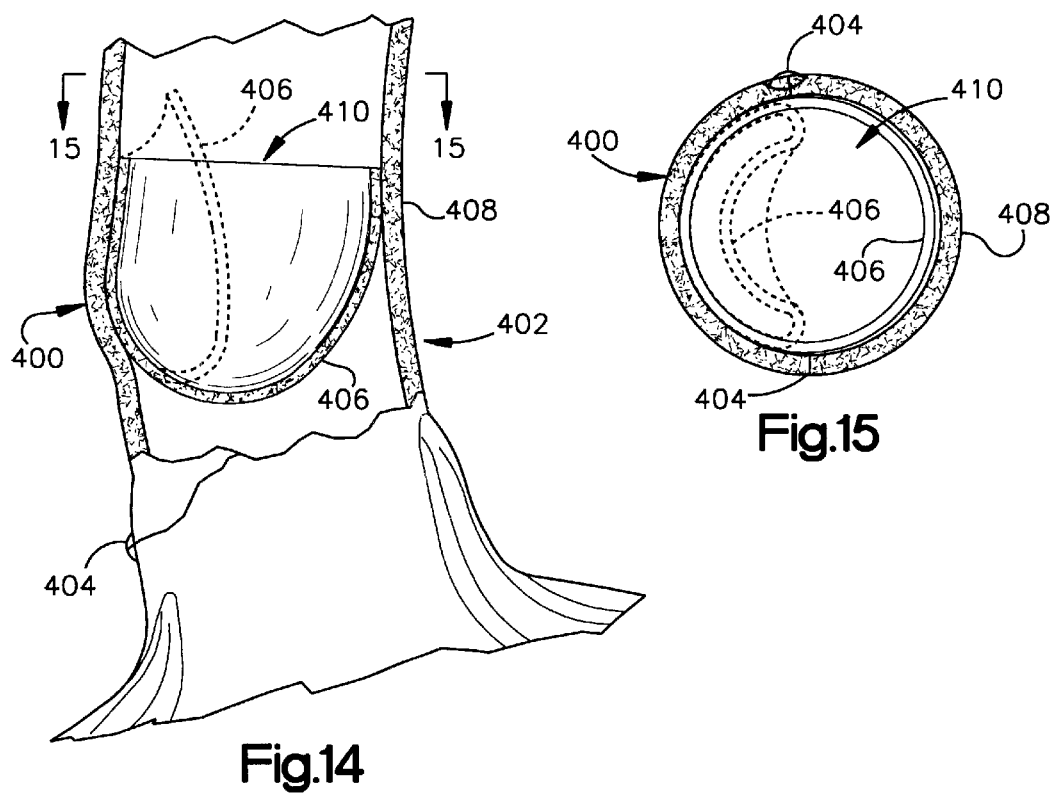
Fig.14
Fig.15

IMPLANTABLE PATCH PROSTHESIS HAVING ONE OR MORE CUSPS FOR IMPROVED COMPETENCY

TECHNICAL FIELD

The present invention relates to implantable devices and, more particularly to an implantable patch prosthesis having one or more cusps to improve competency of a heart valve.

BACKGROUND

Congenital heart abnormalities, in the absence of appropriate surgical treatment, often result in an extremely poor life expectancy and/or quality of life. One particular abnormality is commonly referred to tetralogy of Fallot, which causes anatomic variability in the pulmonary outflow tract and pulmonary arteries. Some anatomic variations stemming from tetralogy of Fallot appear at infancy, such as stenosis at the pulmonary annulus, which may be associated with hypoplasia of the main pulmonary artery. Such anatomic variations may cause severe hypoxemia. Other anatomic variations associated with tetralogy of Fallot may not manifest symptoms until later in childhood, which may include infundibular stenosis with mild or no stenosis at the pulmonary arteries or branch pulmonary arteries.

If tetralogy of Fallot is left untreated, the pulmonary artery system may not develop sufficiently to accommodate total cardiac output, which is due to closure of the ventricular septal defect. This often causes right ventricular failure and mortality resulting from low cardiac output.

Several surgical techniques have been developed to help repair obstructions of the right ventricular outflow tract (RVOT), such as may be associated with tetralogy of Fallot. These may include palliative procedures and total correction, depending on the particular circumstances associated with the patient's condition. Though it is most common for total correction to be utilized.

Total correction usually is implemented during a repair procedure in which an incision is cut in the pulmonary artery extending to the muscular part of the heart. A patch of a biocompatible material (e.g., synthetic or natural tissue) patch is applied across the pulmonary outflow annulus to relieve outflow obstruction. Because the patch passes through the pulmonic valve, which was cut by the incision, however, the valve tends to become insufficient. This has become acceptable, as a stenotic valve is more deleterious to a patient's health and cardiac condition than a regurgitating (e.g., insufficient) valve.

As this practice has continued for many years, studies have indicated that a negative impact associated with pulmonary insufficiency after repair of tetralogy of Fallot. It has also been determined that a competent pulmonic valve is important for the normal growth of a child and the normal function of the pulmonic valve is important.

In an effort to alleviate pulmonary insufficiency, some surgeons are utilizing a patch that has a pericardial cusp formed thereon as part of RVOT reconstruction. The cusp, which is usually formed during the surgical procedure by fixation of the pericardium in a glutaraldehyde solution, is provided to compensate for the damaged cusp(s). This approach is not completely satisfactory as the cusp typically does not last. More particularly, the cusp is not designed so as to assure competency of the pulmonic valve.

SUMMARY

The present invention relates to a cardiac patch prosthesis having one or more cusps. The patch prosthesis includes at least one cusp extending from a length of an associated valve wall. An elongated sheet of biocompatible material is attached to the valve wall, such that a portion of the elongated sheet extends beyond an inflow end of the cusp. A measurement system may be employed to measure the size of a patient's native cusp(s), which measurement may be utilized to select a patch prosthesis having an appropriately sized cusp.

The measurement system includes at least two sizing tools (the number corresponding to the number cusps of a heart valve being constructed). Each of the sizing tools has a generally spherical end portion insertable into and dimensioned to measure size of a cusp. The end portions of the sizing tools are configured to engage each other and form a composite structure having a generally circular cross-section having a predetermined diameter that provides an indication of the size of the heart valve being constructed from the patch prosthesis and the native cusp(s).

BRIEF DESCRIPTION OF THE DRAWINGS

To the accomplishment of the foregoing and related ends, certain illustrative aspects of the invention are described herein in connection with the following description and the annexed drawings. These aspects are indicative, however, of but a few of the various ways in which the principles of the invention may be employed and the present invention is intended to include all such aspects and their equivalents. Other advantages and novel features of the invention will become apparent from the following detailed description of the invention when considered in conjunction with the drawings, in which:

FIG. 1 is an isometric view of a single cusp prosthesis in accordance with the present invention;

FIG. 2 is cross-sectional view taken along line 2—2 of FIG. 1;

FIG. 2A is a cross-sectional view, similar to FIG. 2, illustrating another example of a prosthesis in accordance with the present invention;

FIG. 2B is a cross-sectional view, similar to FIG. 2, illustrating yet another example of a prosthesis in accordance with the present invention;

FIG. 3 is an isometric view of a double cusp prosthesis in accordance with the present invention;

FIG. 4 is an isometric view of cusp measurement system in accordance with the present invention;

FIG. 5 is an exploded view of a cusp measurement system in accordance with the present invention;

FIG. 9 illustrates a heart after a completed procedure in accordance with the present invention;

FIG. 13 is a cross-sectional view of an implanted double cusp prosthesis in accordance with the present invention;

FIG. 14 is a side-sectional view of a single cusp prosthesis that has been implanted in accordance with the present invention; and FIG. 15 is a cross-sectional view taken along line 15—15 of FIG. 14.

DESCRIPTION OF THE INVENTION

Figure 8:
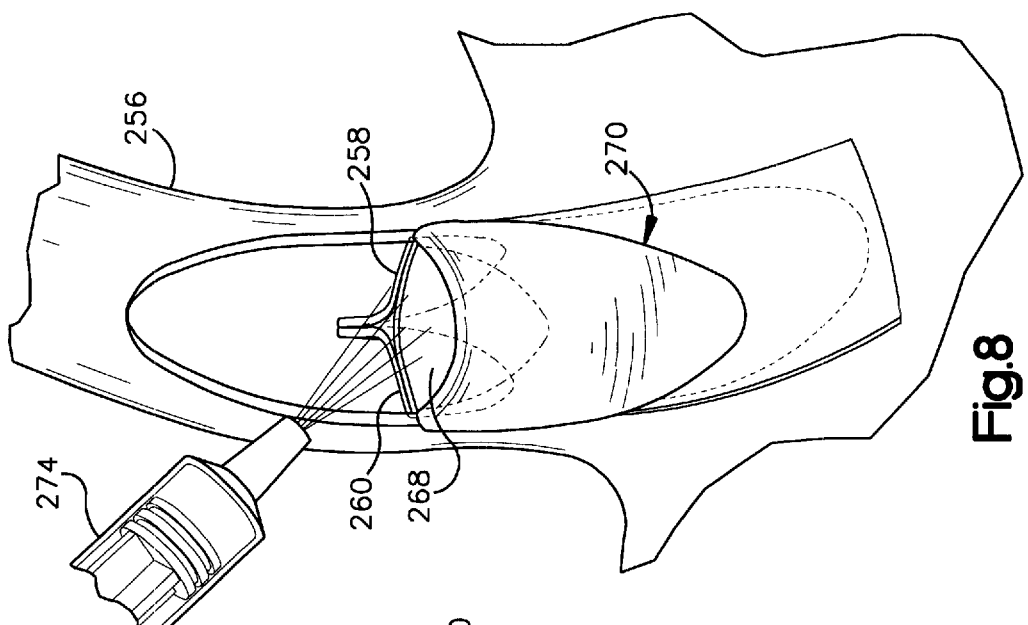
FIG. 8 illustrates a single cusp prosthesis being implanted in accordance with the present invention.

The present invention provides a system and method to improve competence of a heart valve. A patch having one or more cusps is selected such that the cusp(s) of the patch cooperate with part of the recipient's tissue (e.g., the valve wall or native cusp(s)) to provide a competent valve. While the following description and related drawings relate to using the valve to facilitate reconstruction of a right ventricular outflow tract, those skilled in the art will understand and appreciate that the system and method described herein is applicable to help repair other valves.

Turning now to FIGS. 1 and 2, a single cusp prosthesis 10 in accordance with an aspect of the present invention is illustrated. The prosthesis 10 includes a cusp 12 that extends from an associated sheet of valve wall 14. The valve wall 14 is slightly curved about its long axis around the cusp 12, such as corresponding to the contour of the valve wall from which it was excised. An elongated sheet of a biocompatible, flexible material 16 is secured (e.g., by sutures 18 and/or a surgical adhesive) to a side 20 of the valve wall 14 opposite to the side 22 from which the cusp 12 extends. The sheet 16 also may be slightly curved by conforming to the curved valve wall 14.

In this example, one end 24 of the sheet 16 is positioned intermediate an open end 26 of the cusp 12 and an adjacent end 28 of the valve wall 14. Another end 30 of the sheet 16 extends beyond another end 32 of the valve wall 14 opposite from the end 28, such that the overall length of the prosthesis 10 is increased. Side edges of the sheet 16 and the valve wall 14 may be substantially aligned and connected together as shown in FIG. 1.

In accordance with an aspect of the present invention, the sheet 16 is formed of animal pericardium (e.g., bovine, equine, porcine, etc.). For example, the sheet 16 may be a sheets of a NO-REACT® pericardial patch, which is commercially available from Shelhigh, Inc., of Millburn, N.J. The NO-REACT® pericardial patch helps improve the biocompatibility of the resulting prosthesis, thereby mitigating the likelihood of a patient rejecting the implanted prosthesis 10. The NO-REACT® pericardial patch also resists calcification. It is to be understood and appreciated that other types of biocompatible sheets (e.g., natural or synthetic, also may be utilized in accordance with the present invention.

By way of further example, the cusp 12 and valve wall 14 are formed from a heart valve, such as a porcine pulmonic valve, which has been excised from a donor animal, trimmed, and fixed in a suitable solution (e.g., glutaraldehyde). The heart valve may have been and chemically treated in a manner similar to the pericardial patch that forms the inflow-extending sheet 16. The excised valve is opened, such as by cutting axially through the valve wall and one of the valve cusps. For example, the posterior cusp may be sacrificed via the incision, such that an anterior cusp and/or a second semilunar cusp remain intact along the interior of the valve wall. The resulting sheet of valve wall having one or more cusps thereon is trimmed to a desired configuration to form the prosthesis 10 shown in FIGS. 1 and 2.

FIG. 2A is a cross-sectional view of another example of patch prosthesis 34 in accordance with an aspect of the present invention. The prosthesis 34 has a similar configuration to the prosthesis 10 of FIGS. 1 and 2, in that it includes one or more flexible cusp 35 that extends from an associated sheet of valve wall 36. The valve wall 36 has been trimmed, such that opposed ends 37 and 38 extend a small amount (if any) beyond the periphery of the cusp 35. The valve wall 36 is secured (e.g., by sutures and/or a surgical adhesive) to an elongated sheet 39 of a biocompatible, flexible material. The sheet 39 has opposed ends 40 and 41, each of which extends a length beyond an adjacent end 37, 38 of the valve wall 36. For example, the integral assembly of the cusp 35 and valve wall 36 is located approximately midway between the ends 40 and 41 of the sheet 39.

FIG. 2B illustrates yet another example of a patch prosthesis 42 in accordance with an aspect of the present invention. The prosthesis 42 includes one or more flexible cusp 43 that extends from an associated sheet of valve wall 44. The valve wall 44 may be slightly curved about the cusp 43 according to the contour of the heart valve from which the section of valve wall and cusp have been excised. In this example, more than one elongated sheet (e.g., two or more sheets) 45 and 46 of a biocompatible, flexible material are secured together and to the valve wall 44, as shown in FIG. 2B. More than one sheet 45 and 46 may be desired to form the inflow extension of the prosthesis 42, for example, when each sheet has a thickness that is less than may be desired for the inflow extension (e.g., if formed of porcine pericardium).

It is to be appreciated that various combinations of features and permutations based on the examples of FIGS. 2, 2A and 2B could be utilized to form a prosthesis in accordance with an aspect of the present invention. Those skilled in the art also will understand and appreciated that the prostheses illustrated in FIGS. 2A and 2B may be formed from materials substantially similar to that described above with respect to FIGS. 1 and 2.

FIG. 3 illustrates an example of another patch prosthesis 50 in accordance with an aspect of the present invention. The prosthesis 50 is similar to the monocusp prosthesis 10 shown and described with respect to FIGS. 1 and 2, but includes a pair of cusps 52 and 54 that extend from a common side 56 of a sheet of tissue 58, such as valve wall. An elongated sheet 60 of a biocompatible, flexible material is secured (e.g., by sutures 62 and/or a surgical adhesive) to another side 64 of the valve wall 58 opposite to the side 56.

One end 66 of the sheet 60 is positioned intermediate an outflow end 68 of the cusps 52 and 54 and an adjacent end 70 of the valve wall 58. Another end 72 of the sheet 60 extends beyond an opposite end 74 of the valve wall 58, such that the overall length of the prosthesis 50 is increased by an inflow extension formed of the sheet 60.

It is to be understood and appreciated by those skilled in the art that the sheet 60 and valvular assembly of the valve wall 58 and cusps 52 and 54 may be formed of in a substantially similar manner and from materials as previously described with respect to FIGS. 1 and 2. Those skilled in the art will perceive manufacturing and design variations, including features shown and described with respect to FIGS. 2A and 2B, as well as the other types of tissues (e.g., natural or synthetic) that may be utilized to form the bicusp prosthesis 50, all of which are contemplated as being within the scope of the present invention.

It further is to be appreciated that the dimensions and configuration of the prostheses 10 and 50 may vary according to the requirements of the patient for which they are intended. FIGS. 4 and 5 illustrate a measurement system 100 that may be utilized to measure cusp sizes to help provide a competent valve in accordance with an aspect of the present invention. In this example, the measurement system 100 is formed of three cusp sizing tools 102, 104, and 106. As shown in FIG. 4, the sizing tools 102, 104, and 106 are dimensioned and configured as having mating pie-shaped wedges that engage each other to form a generally circular cylindrical system 100 having a predetermined diameter, such as may approximate a diameter of a tubular valve wall of a corresponding heart valve. Typically, a plurality of such measurement systems 100 are provided so that a surgeon may determine a desired cusp size for an implantable patch prosthesis 10, 50 (FIG. 1, FIG. 3).

Each tool 102, 104, 106 in the system 100 includes an associated sizer 108, 110, 112 having a generally spherical configuration adapted to fit into a cusp having a size generally equal to or larger than the respective sizer. In order to facilitate insertion of each sizer 108, 110, 112 into a cusp, an elongated handle 114, 116, 118 extends outwardly from each respective sizer. A surgeon grips the handle to insert a sizer into a cusp to measure its corresponding size. The measurement process may repeated with measurement systems having differently sized sizers 108, 110, 112 to determine an appropriate size of cusp(s) needed for a patch prosthesis in accordance with the present invention. Once the size of patient's remaining cusp or cusps is determined, a suitable patch prosthesis (e.g., prosthesis 10, 34, 42 or 50 shown in FIGS. 1, 2A, 2B or FIG. 3, respectively) having a desired cusp size may be selected, such as by utilizing an appropriately sized measurement tool 102–106. As a result, the selected patch has one or more cusps that cooperate with the patient's native tissue (e.g., the remaining cusp(s) and/or valve wall) to provide a functional and substantially competent valve. It is to be appreciated that when the patch is implanted, the prosthetic cusps cooperate with the native cusps to provide a circular cross-section, even if each cusp has a different size.

By way of example, the cusp sizers 108, 110, and 1 12 may be formed of a molded or cut plastic or rubber material. The handles 114, 116, and 118 may be formed of any generally rigid material (e.g., a plastic-like material, metal, etc.). It is to be understood and appreciated that other materials also could be utilized to form the sizers 108, 110, and 112 and handles 114, 116, and 118.

It is to be appreciated that the measurement system 100 may be employed to measure cusp sizes for implanting various types of patches, including those disclosed herein as well as other types and configurations of patches.

FIGS. 6–9 illustrate an example of a procedure that may be utilized to implant a patch having a single cusp in accordance with an aspect of the present invention. While the following discussion generally relates to implanting the patch at the right ventricular outflow tract, it is to be appreciated that a patch prosthesis, in accordance with the present invention, could be implanted at other locations.

Figure 6:
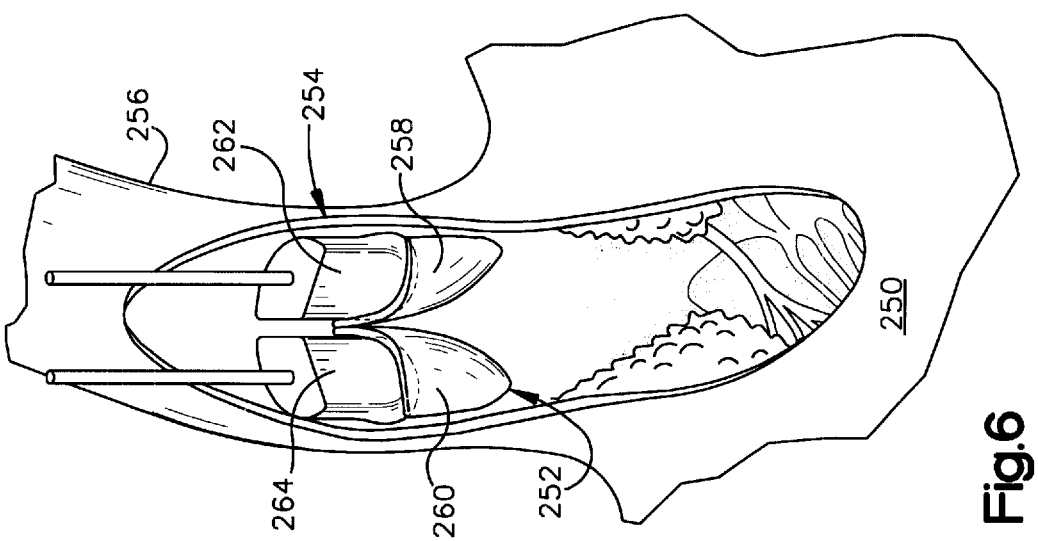
FIG. 6 illustrates part of a surgical procedure in which a recipient's cusps are measured in accordance with the present invention.

FIG. 6 illustrates part of a heart 250 after performing a ventriculotomy, in which an incision is made into the right ventricular muscle just below the pulmonic valve 252 at the right ventricular outflow tract 254. The incision may be extended across the annulus onto the pulmonary artery 256 as far as deemed necessary. The incision passes through the anterior semilunar cusp (not shown), thereby damaging the cusp. The pulmonic valve 252 usually has three cusps, but sometimes it has two cusps.

After extending the incision over the valve 252 and the pulmonary artery 256, the damaged cusp(s) is removed and the pulmonic wall is cut near both commissures of the remaining cusps 258 and 260. The remaining cusp or cusps 258 and 260 are sized with sizing tools 262 and 264, such as shown and described above with respect to FIGS. 4 and 5. After sizing the native cusps 258 and 260, the measurements are utilized to select a patch prosthesis having an appropriately sized cusp, in accordance with an aspect of the present invention.

Figure 7:
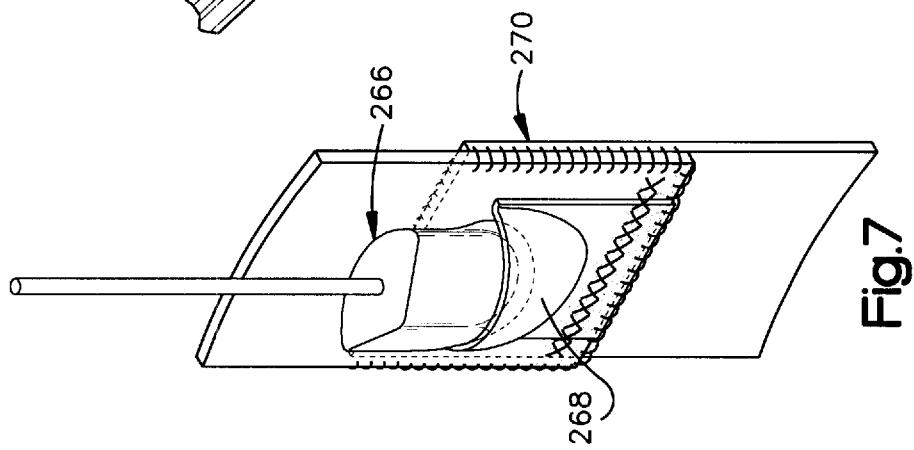
FIG. 7 illustrates a corresponding measurement being taken for a cusp of a prosthesis in accordance with the present invention.

As shown in the example of FIG. 7, another sizing tool 266 is utilized to measure the size of a cusp 268 of a monocusp patch prosthesis 270 in accordance with an aspect of the present invention. In particular, the sizing tools 262, 264, and 266 form a measurement system 100 (FIGS. 4 and 5) operative to measure cusp sizes to facilitate reconstruction of the pulmonic valve. The resulting valve will have a diameter corresponding to the diameter of the measurement system and is formed of the patient's native cusps 258 and 260 and the cusp 268 of the monocusp patch. The measurement system thus enables the resulting valve to have a desired diameter and competency. While the prosthesis 270 is shown to be similar in configuration to the example of FIGS. 1 and 2, those skilled in the art will understand and appreciate that other versions (e.g., as shown in FIG. 2A or 2B) could also be utilized.

With reference to FIG. 8, once size has been chosen, the selected patch prosthesis 270 is mounted at the incision. For example, a pair of sutures is applied to opposite sides of the cusp 268 to bring the commissures of the cusp 268 into a desired position relative to the patient's native cusps 258 and 260. A syringe 274 or other appropriate pump system is utilized to test the competency of the resulting valve. The syringe applies fluid (e.g., water or a saline solution) at the outflow of the cusps, which fills the cusps and causes coaptation. The surgeon then is able to determine whether the coaptation between the cusps 258, 260 and 268 is satisfactory. If the amount of coaptation is unsatisfactory or the placement of the cusp 268 appears inappropriate for any reason, the surgeon may adjust the position of the patch and retest the valve in a similar manner.

Once a desired result is achieved, the surgeon may complete the procedure. The monocusp patch 270 is trimmed according to the "wound to be covered." The perimeter of the patch 270 is then secured (e.g., by sutures 276) relative to the incision opening to complete the procedure, such as shown in FIG. 9. As a result, the patch 270 operates to widen the infundibular and improve the hemodynamics at the outflow of the right ventricle. In addition, the patch 270 mitigates stenosis and regurgitation associated with the pulmonic valve. The native tissue at the pulmonic valve also may continue to grow, thereby significantly reducing the likelihood of re-operation.

Figure 10:
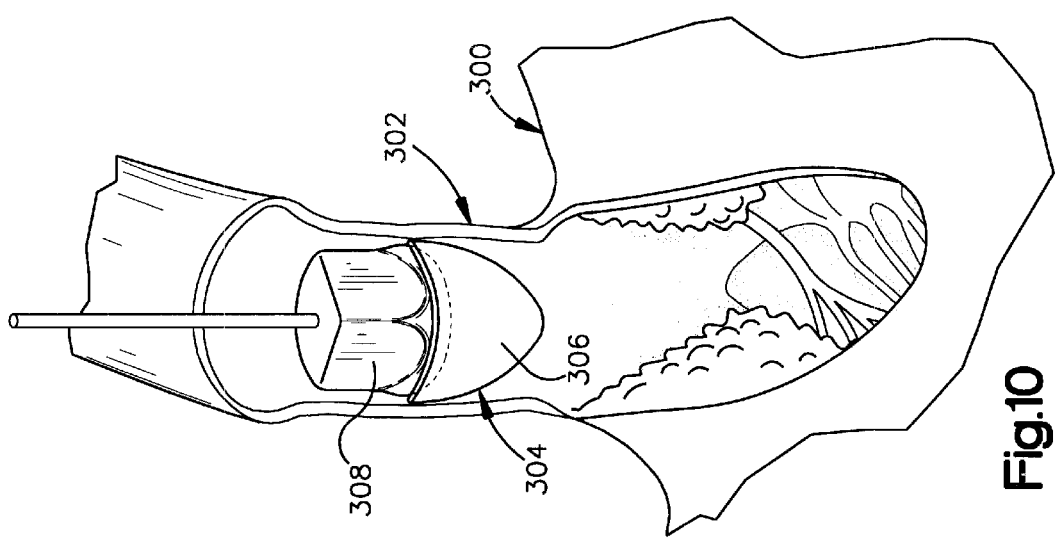
FIG. 10 illustrates part of a surgical procedure in which a recipient's cusp is measured in accordance with the present invention.

FIGS. 10, 11, 12 and 13 illustrate another example of a procedure that may be utilized to implant a patch having a double cusp in accordance with an aspect of the present invention. FIG. 10 illustrates a portion of a heart 300 after having performed a ventriculotomy at the right ventricular outflow tract 302 and into the part just below the pulmonic valve 304. In this example, only one good native cusp 306 remains after the incision. A cusp measurement tool 308 is utilized to measure the size of the cusp 306. The measurement with the tool 308 may then be utilized to select a patch having an appropriately sized cusp or cusps, such that the resulting valve has a corresponding diameter as determined by a measurement system of which the tool 308 is part.

Figure 11:
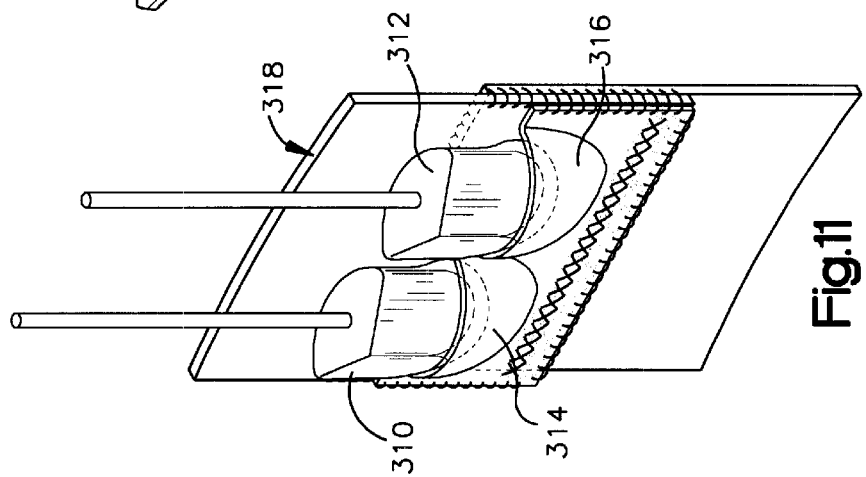
FIG. 11 illustrates a prosthesis being measured in accordance with the present invention.

As shown in FIG. 11, corresponding measurement tools 310 and 312 are utilized to measure the size of respective cusps 314 and 316 in a patch prosthesis 318 in accordance with an aspect of the present invention. As a result, the cusps 314 and 316 are able to cooperate (or coapt) with the native cusp 306 (FIG. 10), so as to form a complete and competent tricuspid pulmonic valve.

Figure 12:
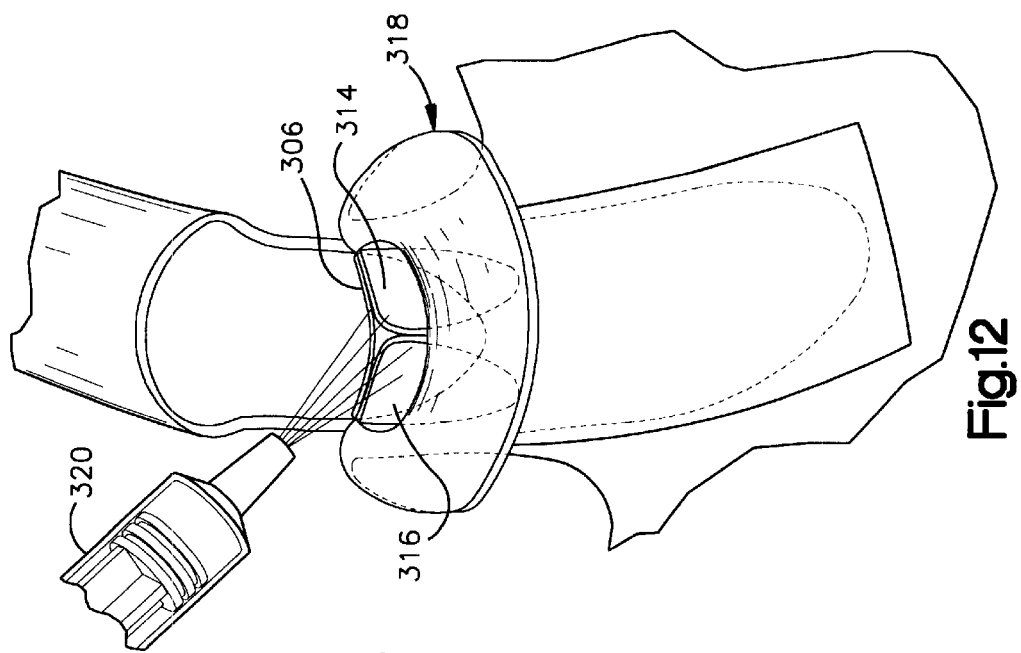
FIG. 12 illustrates a double-cusp prosthesis being implanted in accordance with the present invention.

As shown in FIG. 12, the selective patch prosthesis 318 is positioned such that the commissures of the cusps 314 and 316 align with the commissures of the native cusp 306. Initially, one or more temporary sutures may be utilized to hold the cusps 314 and 316 relative to the native cusp 306. The patch cusps 314 and 316 may then be moved into position and further tied temporarily such that the valve may be tested for competency. For example, a syringe or other suitable applicator 320 may apply a saline solution onto the outflow of the cusps 306, 314, 316 to ensure an appropriate level of valve competency. If the valve is competent and cooptation between the cusps 314, 316 and 306 is adequate, the procedure may be completed by securing the periphery of the prosthesis 318 relative to the incision, such as shown and described with respect to FIG. 9.

FIG. 13 illustrates a cross-sectional outflow view of an implanted bicusp patch prosthesis 350 and pulmonary tract 352. As mentioned above, the prosthesis includes a valve wall 354 from which a pair of cusps 356 and 358 extend. A native cusp 360 similarly extends from associated valve wall of the patient's outflow tract (e.g., pulmonary artery) 352. The cusps 356, 358 and 360 are illustrated in a closed condition, in which they coapt in a desired manner. The valve, which is formed by the cusps 356, 358 and 360, has a generally circular cross section having a diameter defined by the width 362 of the patch 350 and the length of the remaining arc of the patient's pulmonary artery 352. The width 362 of the patch 350 is better illustrated from the phantom depiction of the prosthesis 350, in which the prosthesis has been unattached and generally straightened relative to the pulmonary artery 352.

The implanted prosthesis 350 has its side edges secured relative to the pulmonary artery by sutures 364. Advantageously, the cusps 356 and 358 of the prosthesis 350 cooperate with the native cusp 360 to provide a competent valve having desirable cooptation. As a result, regurgitation of the cusps 356, 358, 360 is mitigated and the outflow of blood is improved due to the increased diameter of the resulting valve. In addition, the native portions of the outflow tract can continue to grow which is particularly desirable in situations when implanted in small children and infants.

FIGS. 14 and 15 illustrate another example of a monocusp patch prosthesis 400 that has been implanted at a right ventricular outflow tract 402 in accordance with an aspect of the present invention. The prosthesis 400 is secured to the outflow tract by sutures 404. The prosthesis 400 includes a single cusp 406, which cooperates with the pulmonic valve wall 408 of the patient to form a pulmonic valve, indicated at 410. Each of the FIGS. 14 and 15 illustrates the cusp 406 of the valve 410 in an open condition (by dotted lines) and in a closed condition (by solid lines). In this example, the monocusp patch prosthesis 400 is selected such that its cusp 406 is sufficiently large (e.g., has a diameter at least equal to the diameter of the pulmonary artery defined by the width of the patch prosthesis 400 and the arc length of the remaining native pulmonic valve wall 408.

It is to be understood and appreciated that such a monocusp patch prosthesis 400 may be utilized in situations when no remaining native cusps are available, such as when all cusps have been damaged by the incision or through other defects, or in the absence of a pulmonic valve. It is to be appreciated that the use of a patch prosthesis 400, in accordance with an aspect of the present invention mitigates stenosis of the pulmonic valve. In addition, the patch prosthesis 400 also reduces the risk of regurgitation and completes a competent valve.

What has been described above includes examples of the present invention. It is, of course, not possible to describe every conceivable combination of components or methodologies for purposes of describing the present invention, but one of ordinary skill in the art will recognize that many further combinations and permutations of the present invention are possible. Accordingly, the present invention is intended to embrace all such alterations, modifications and variations that fall within the spirit and scope of the appended claims.

What is claimed is:

1. A cardiac patch prosthesis, comprising:
   at least one cusp extending from a length of an associated valve wall; and
   an elongated sheet of biocompatible material, the valve wall being attached to the elongated sheet, such that a portion of the elongated sheet extends beyond an inflow end of the cusp, whereby, upon implanting the patch prosthesis in a recipient's heart, the at least one cusp is adapted to cooperate with at least one of a native cusp and a native valve wall of the recipient to provide a substantially competent heart valve.

2. The prosthesis of claim 1, wherein the at least one cusp further comprises two cusps extending from the associated valve wall.

3. The prosthesis of claim 1, wherein the valve wall is part of a valve wall of an animal pulmonic heart valve and the at least one cusp is a cusp of the pulmonic heart valve.

4. The prosthesis of claim 1, wherein the valve wall is part of a valve wall of an animal aortic heart valve and the at least one cusp is a cusp of the aortic heart valve.

5. The prosthesis of claim 1, further comprising sutures located near inflow and outflow ends of the at least one cusp to attach the valve wall relative to the elongated sheet.

6. The prosthesis of claim 5, wherein the sutures located near the outflow end of the at least one cusp extend through the elongated sheet and partially through valve wall.

7. The prosthesis of claim 1, wherein an outflow end portion of the valve wall extends a length beyond an outflow end of the elongated sheet.

8. A cardiac patch prosthesis and measurement system, comprising:
   at least one cusp extending from a length of an associated valve wall; and
   an elongated sheet of biocompatible material, the valve wall being attached to the elongated sheet, such that a portion of the elongated sheet extends beyond an inflow end of the cusp; and
   a plurality of measurement tools, at least one of the measurement tools having a generally spherical end portion insertable into and adapted to measure size of the at least one cusp and another of the measurement tools having a generally spherical end portion insertable into adapted to measure size of at least one native cusp of an intended recipient of the prosthesis.

9. A repair system, comprising:
   a patch prosthesis including an elongated sheet of a biocompatible flexible material and at least one cusp extending outwardly from and moveable relative to the elongated sheet; and a measurement system including at least two sizing tools, each of the sizing tools having a generally spherical end portion insertable into and adapted to measure size of a cusp, the end portions of the sizing tools being configured to engage each other and provide a generally cylindrical structure having a generally circular cross-section having a predetermined diameter.

10. The system of claim 9, wherein the prosthesis further comprises a length of a valve wall from which the at least one cusp extends outwardly, the valve wall being attached to the elongated sheet.

11. The system of claim 10, wherein the at least one cusp further comprises two cusps extending from the length of valve wall.

12. The system of claim 10, wherein the prosthesis further comprises sutures located near inflow and outflow ends of the at least one cusp to attach the valve wall relative to the elongated sheet.

13. The system of claim 12, wherein the sutures located near the outflow end of the at least one cusp extend completely through the elongated sheet and partially through the valve wall.

14. The system of claim 10, wherein an outflow end portion of the valve wall extends a length beyond an outflow end of the elongated sheet.

15. The system of claim 9, wherein the at least two sizing tools further comprises three sizing tools, each of the sizing tools having an end portion dimensioned and configured to engage the other two sizing tools as a sectional part of the cylindrical structure.

16. The system of claim 15, wherein each of the sizing tools further comprises a handle extending from the end portion thereof.

17. A cardiac patch prosthesis, comprising:
an elongated sheet of a flexible, biocompatible material;
flexible cup-shaped means attached to and extending from an associated valve wall for moving between open and closed conditions relative to the valve wall; and
means for connecting the cup-shaped means and valve wall relative to the elongated sheet, whereby, upon implanting the patch prosthesis in a recipient's heart, the at least one cusp is adapted to cooperate with at least one of a native cusp and a native valve wall of the recipient to provide a substantially competent heart valve.

18. A measurement system to facilitate repair of a heart valve, comprising:
at least two sizing tools, each of the sizing tools having a generally spherical end portion and a handle extending therefrom, each end portion being insertable into and dimensioned to measure size of a cusp, the end portions of the sizing tools being configured to engage each other and form a generally cylindrical structure having a generally circular cross-section having a predetermined diameter.

19. The system of claim 18, wherein the at least two sizing tools further comprises three sizing tools, each of the sizing tools having an end portion dimensioned and configured to engage the other two sizing tools as a sectional part of the cylindrical structure.

20. A method to facilitate repair of a heart valve comprising:
inserting a first sizing tool into a native cusp of the heart valve to measure the size of the native cusp; and
inserting at least a second sizing tool into a cusp of a patch prosthesis to measure the size of the cusp of the patch relative to the size of the native cusp, the first and second sizing tools having end portions configured to engage each other and form a generally cylindrical structure having a generally circular cross-section having a predetermined diameter approximating a cross-sectional diameter of the heart valve.

21. The method of claim 20, wherein prior to inserting the sizing tool into the cusp of the patch, the method further comprises inserting a third sizing tool into a second native cusp of the patient, each of the three sizing tools having an end portion dimensioned and configured to engage the other sizing tools as a sectional part of the cylindrical structure.

22. The method of claim 20, further comprising temporarily mounting the patch over the native cusp, such that commissures of the native cusp align with commissures of the cusp of the patch and applying fluid at an outflow end of the cusps to test competency of a resulting heart valve.

23. The method of claim 20, wherein the cusp of the patch prosthesis further comprises two cusps that extend from an associated valve wall.

24. The method of claim 23, further comprising inserting a third sizing tool into a second cusp of the patch prosthesis to measure the size of the second cusp of the patch relative to the native cusp, each of the three sizing tools having an end portion dimensioned and configured to engage the other sizing tools as a sectional part of the cylindrical structure.

* * * * *